(12) United States Patent
D'Ambrosio et al.

(10) Patent No.: US 12,268,861 B2
(45) Date of Patent: *Apr. 8, 2025

(54) BLOOD PUMP ASSEMBLY HAVING A SENSOR AND A SENSOR SHIELD

(71) Applicant: ABIOMED, Inc., Danvers, MA (US)

(72) Inventors: Ralph Louis D'Ambrosio, Danvers, MA (US); Bruce Adams, Danvers, MA (US); Michael Thomas Finnegan, Danvers, MA (US); Gerd Spanier, Aachen (DE); Thorsten Siess, Aachen (DE)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/385,426

(22) Filed: Oct. 31, 2023

(65) Prior Publication Data
US 2024/0139496 A1 May 2, 2024

Related U.S. Application Data

(60) Division of application No. 17/308,246, filed on May 5, 2021, now Pat. No. 11,844,940, which is a
(Continued)

(51) Int. Cl.
*A61B 5/0215* (2006.01)
*A61M 60/13* (2021.01)
(Continued)

(52) U.S. Cl.
CPC .......... *A61M 60/148* (2021.01); *A61M 60/13* (2021.01); *A61M 60/174* (2021.01);
(Continued)

(58) Field of Classification Search
CPC .......... A61M 2205/3334; A61M 60/13; A61M 60/148; A61M 60/174; A61M 60/216;
(Continued)

(56) References Cited

U.S. PATENT DOCUMENTS

| 4,945,230 A | 7/1990 | Saaski et al. |
| 5,645,531 A | 7/1997 | Thompson et al. |
| (Continued) | | |

FOREIGN PATENT DOCUMENTS

| CA | 2576978 A1 | 3/2006 |
| CA | 2591787 A1 | 6/2006 |
| (Continued) | | |

OTHER PUBLICATIONS

International Search Report for PCT/US2017/036117 dated Jan. 9, 2017 (3 pages).
(Continued)

*Primary Examiner* — Jon Eric C Morales
(74) *Attorney, Agent, or Firm* — Botos Churchill IP Law LLP

(57) ABSTRACT

A blood pump assembly can include various components such as a housing and a sensor configured to detect one or more characteristics of the blood. In some embodiments, the sensor can be coupled to the housing and can include a sensor membrane configured to deflect in response to a change in a blood parameter (e.g., pressure). The blood pump assembly can include a shield that covers at least a portion of the sensor membrane so as to protect the sensor from damage when the blood pump assembly is inserted through an introducer and navigated through the patient's vasculature and/or when the blood pump assembly is inserted into the heart in a surgical procedure. One or more protective layers can be deposited over the sensor membrane to prevent the sensor membrane from being dissolved through interactions with the patient's blood.

11 Claims, 9 Drawing Sheets

Related U.S. Application Data continuation of application No. 16/433,138, filed on Jun. 6, 2019, now Pat. No. 11,027,114, which is a continuation of application No. 15/615,259, filed on Jun. 6, 2017, now Pat. No. 10,342,906.

(60) Provisional application No. 62/346,163, filed on Jun. 6, 2016.

(51) Int. Cl.
  *A61M 60/148* (2021.01)
  *A61M 60/174* (2021.01)
  *A61M 60/216* (2021.01)
  *A61M 60/414* (2021.01)
  *A61M 60/546* (2021.01)
  *A61M 60/816* (2021.01)

(52) U.S. Cl.
  CPC ........ *A61M 60/216* (2021.01); *A61M 60/414* (2021.01); *A61M 60/546* (2021.01); *A61M 60/816* (2021.01); *A61M 2205/3334* (2013.01)

(58) Field of Classification Search
  CPC . A61M 60/414; A61M 60/546; A61M 60/816
  See application file for complete search history.

(56) References Cited

U.S. PATENT DOCUMENTS

| | | | |
|---|---|---|---|
| 5,911,685 | A | 6/1999 | Siess et al. |
| 5,964,694 | A | 10/1999 | Siess et al. |
| 6,176,822 | B1 | 1/2001 | Nix et al. |
| 6,295,877 | B1 | 10/2001 | Aboul-Hosn et al. |
| 6,398,738 | B1 | 6/2002 | Millar |
| 7,022,100 | B1 | 4/2006 | Aboul-Hosn et al. |
| 7,259,862 | B2 | 8/2007 | Duplain |
| 7,689,071 | B2 | 3/2010 | Belleville et al. |
| 8,752,435 | B2 | 6/2014 | Belleville et al. |
| 10,342,906 | B2 | 7/2019 | D'Ambrosio et al. |
| 11,027,114 | B2 * | 6/2021 | D'Ambrosio ....... A61M 60/216 |
| 2001/0051030 | A1 | 12/2001 | Hoefner |
| 2003/0187322 | A1 | 10/2003 | Siess |
| 2004/0022640 | A1 | 2/2004 | Siess et al. |
| 2009/0074367 | A1 | 3/2009 | Shinoski et al. |
| 2010/0241008 | A1 | 9/2010 | Belleville et al. |
| 2015/0141842 | A1 | 5/2015 | Spanier et al. |
| 2015/0290372 | A1 | 10/2015 | Muller et al. |

FOREIGN PATENT DOCUMENTS

| | | |
|---|---|---|
| CA | 2819564 A1 | 9/2012 |
| CN | 100451694 C | 1/2009 |
| EP | 1911484 A2 | 4/2008 |
| EP | 2638375 A4 | 10/2014 |
| JP | 2005291945 A | 10/2005 |
| JP | 4994244 B2 | 5/2012 |
| JP | 2012520690 A | 9/2012 |
| JP | 5264172 B2 | 5/2013 |
| JP | 2015514529 A | 5/2015 |
| WO | 20000037139 | 6/2000 |
| WO | 01074419 | 10/2001 |
| WO | 0247751 A2 | 6/2002 |
| WO | 2006032128 A1 | 3/2006 |
| WO | 2006066393 A1 | 6/2006 |
| WO | 2011039091 A1 | 4/2011 |
| WO | 2013160407 A1 | 10/2013 |
| WO | 2015160943 A1 | 10/2015 |
| WO | 2017137578 A1 | 8/2017 |

OTHER PUBLICATIONS

Office Action for Australian Application No. 2017279518 dated Jun. 2, 2021 (4 pages).
Office Action for Japanese Application No. 2019-516097 dated Jun. 7, 2021 (8 pages).
Office Action issued in Japanese Patent Application No. 2022-007559 dated Mar. 24, 2022 (8 pp.).
U.S. Appl. No. 60/637,755, filed Dec. 22, 2004 (10 pages).
Office Action issued in corresponding Australian Patent Application No. 2022218599 dated Oct. 17, 2023 (2 pp.).
Written Opinion for International Application No. PCT/US2017/036117 dated Jan. 9, 2016 (6 pages).

* cited by examiner

BLOOD PUMP ASSEMBLY HAVING A SENSOR AND A SENSOR SHIELD

CROSS-REFERENCE TO RELATED APPLICATIONS

This application is a divisional of U.S. patent application Ser. No. 17/308,246, filed May 5, 2021, now U.S. Pat. No. 11,844,940, which is a continuation of U.S. patent application Ser. No. 16/433,138, filed Jun. 6, 2019, now U.S. Pat. No. 11,027,114, which is a continuation of U.S. patent application Ser. No. 15/615,259, filed Jun. 6, 2017, now U.S. Pat. No. 10,342,906, which claims the benefit of U.S. Provisional Application No. 62/346,163, filed Jun. 6, 2016, the disclosures of all of which are hereby incorporated by reference in their entirety.

BACKGROUND OF THE INVENTION

A blood pump assembly, such as an intracardiac blood pump assembly, may be introduced into the heart to deliver blood from the heart into an artery. Various blood pump assemblies pull blood from the left ventricle of the heart and expel blood into the aorta. Some blood pump assemblies may support the left side of the heart and may be introduced percutaneously during a cardiac procedure through the vascular system, such as by a catheterization procedure through the femoral artery, into the ascending aorta, across the aortic valve, and into the left ventricle. In systems intended to support the right side of the heart, blood pump assemblies can be introduced through a vein and inserted into the heart through the venous system (i.e. vena cava). Blood pump assemblies for either side of the heart may also be surgically implanted or inserted through the subclavian and/or carotid arteries.

During insertion of a blood pump assembly through a blood vessel, the torturous path and/or calcified anatomy can obstruct and damage components of the blood pump assembly. Damage to a blood pump assembly during insertion may require removal or replacement of the blood pump assembly. Because the blood pump assembly is designed for use in procedures that impact patient vitality, it is important that the blood pump assembly be capable of precise operation and delivery. Still further, it can be important to monitor the patient's interactions with the blood pump assembly.

SUMMARY OF THE INVENTION

In one aspect, a blood pump assembly includes a blood pump housing component, at least one input port and at least one outlet port, and a sensor coupled to the blood pump housing component. The sensor includes a sensor membrane configured to deflect in response to a change in a blood parameter. The sensor is coupled to a transmission fiber. The blood pump assembly includes a shield that covers at least a portion of the sensor membrane to protect the sensor from physical damage.

In some implementations, the shield includes a barrier bump positioned distal relative to the sensor membrane. In certain implementations, the blood pump assembly further includes a sensor visor to protect the sensor from physical damage, the sensor visor extending in a distal direction beyond the sensor membrane. In some implementations, the sensor visor extends into a visor notch formed in the barrier bump. In certain implementations, the blood pump assembly further includes a cap that covers the visor notch. In some implementations, the sensor visor is attached to the barrier bump by adhesive or welding. In certain implementations, the shield includes at least one protective layer covering a surface of the sensor membrane. In some implementations, the sensor membrane is recessed in a proximal direction relative to the sensor visor. In certain implementations, the shield includes a blood aperture extending through the blood pump housing component and positioned distal relative to the sensor membrane for washing the sensor membrane with blood.

In another aspect, a blood pump assembly includes a blood pump housing component, a cannula assembly coupled to the blood pump housing component, and a sensor coupled to the blood pump housing component. The sensor includes a sensor membrane configured to deflect in response to a change in a blood parameter, and the sensor is coupled to a transmission fiber. The blood pump assembly includes a passive protective mechanism for protecting the sensor from damage when the blood pump assembly is inserted into a patient.

In some implementations, the passive protective mechanism includes a barrier positioned distal to the sensor membrane. In certain implementations, the barrier protrudes from the blood pump housing component. In some implementations, the barrier is composed of the same material as the blood pump housing component. In certain implementations, the barrier has a smooth outer surface which contacts the blood. In some implementations, the barrier has a radial height approximately equal to or greater than a radial height of the sensor. In certain implementations, the blood pump assembly further includes one or more protective layers deposited on a surface of the sensor membrane facing toward a distal end of the blood pump assembly. In some implementations, the one or more protective layers include a single layer deposited over the sensor membrane and formed of a material capable of being deposited as a gel and curing. In certain implementations, the one or more protective layers include a material capable of preventing the sensor membrane from being dissolved by a chemical or biological reaction with blood. In some implementations, the one or more protective layers include a layer of silicone. In certain implementations, the one or more protective layers include a metal oxide. In some implementations, the sensor membrane has a thickness of 2 microns or less. In certain implementations, the sensor is positioned in a sensor bed in the blood pump housing component. In some implementations, the sensor is an optical sensor that transmits optical signals. In certain implementations, the blood pump housing component has a substantially cylindrical and elongate shape.

In another aspect, a blood pump assembly includes a drive unit, an impeller blade, a blood pump housing component, a cannula assembly, and a sensor. The cannula assembly is coupled to the blood pump housing component. The blood pump housing component includes a peripheral wall extending about a rotational axis of the impeller blade. The impeller blade is rotatably coupled to the drive unit. The sensor is coupled to the peripheral wall of the blood pump housing component. The sensor includes a sensor membrane configured to deflect in response to a change in a blood parameter. The sensor membrane is coupled to a transmission fiber. The blood pump assembly includes a shield that covers at least a portion of the sensor membrane.

In some implementations, the shield includes a barrier bump positioned distal relative to the sensor membrane and a sensor visor overhanging the sensor membrane. In certain implementations, the sensor visor extends to the barrier bump. In some implementations, the sensor visor extends into a visor notch in the barrier bump. In some implementations, a cap covers the visor notch. In certain implementations, the sensor visor is attached to the barrier bump by adhesive. In some implementations, the shield includes a protective layer covering a surface of the sensor membrane. In certain implementations, the sensor membrane is recessed further below the sensor visor by a distance approximately equal to the thickness of the protective layer. In some implementations, the shield includes a blood aperture extending through the peripheral wall of the blood pump housing component and positioned distal relative to the sensor membrane for washing the sensor membrane. In certain implementations, the blood aperture is positioned between the sensor membrane and the barrier bump. In some implementations, the sensor visor extends over the blood aperture.

In another aspect, a blood pump assembly includes a drive unit, an impeller blade, a blood pump housing component, a cannula assembly, and a sensor. The cannula assembly is coupled to the blood pump housing component. The blood pump housing component includes a peripheral wall extending about a rotational axis of the impeller blade. The impeller blade is rotatably coupled to the drive unit. The sensor is coupled to the peripheral wall of the blood pump housing component. The sensor includes a sensor membrane configured to deflect in response to a change in a blood parameter. The membrane is coupled to a transmission fiber. The blood pump assembly includes a sensor shield which may be configured as a passive protective mechanism positioned distal relative to the sensor membrane.

In some implementations, the shield (for example, the passive protective mechanism) positioned distal relative to the sensor membrane includes a barrier positioned distal relative to the sensor membrane. In certain implementations, the shield (for example, the barrier) positioned distal relative to the sensor membrane includes a barrier bump positioned distal relative to the sensor membrane. The barrier bump may protrude from the peripheral wall of the blood pump housing component. In certain implementations, the shield (for example, the barrier or barrier bump) is composed of the same material as the blood pump housing component. In some implementations, the shield (for example, the barrier or barrier bump) has a smooth surface. In certain implementations, the shield (for example, the barrier or barrier bump) is composed of stainless steel. In some implementations, the shield (for example, the barrier or barrier bump) is electropolished or mechanically polished. In certain implementations, the shield (for example, the barrier or barrier bump) has a height approximately equal to or greater than the height of the sensor. In some implementations, the shield (for example, the barrier or barrier bump) has a visor notch configured to receive a sensor visor overhanging the sensor membrane.

In certain implementations, the shield of the blood pump assembly includes a passive protective mechanism positioned such that the sensor membrane is positioned between the passive protective mechanism and the peripheral wall of the blood pump housing component. In some implementations, the shield (for example, the passive protective mechanism) positioned such that the sensor membrane is between the shield and the peripheral wall of the blood pump housing includes a barrier positioned such that the sensor membrane is between the barrier and the peripheral wall of the blood pump housing. In certain implementations, the shield (for example, the barrier) positioned such that the sensor membrane is between the shield and the peripheral wall of the blood pump housing includes a sensor visor overhanging the sensor membrane. In some implementations, the sensor visor is stainless steel. In certain implementations, the sensor visor has a smooth surface. In some implementations, the sensor visor includes a biocompatible material. In certain implementations, the sensor visor is coated by a biocompatible material.

In another aspect, a blood pump assembly includes a drive unit, an impeller blade, a blood pump housing component, a cannula assembly, and a sensor. The cannula assembly is coupled to the blood pump housing component. The blood pump housing component includes a peripheral wall extending about a rotational axis of the impeller blade. The impeller blade is rotatably coupled to the drive unit. The sensor is coupled to the peripheral wall of the blood pump housing component. The sensor includes a sensor membrane configured to deflect in response to a change in a blood parameter. The membrane is coupled to a transmission fiber. The blood pump assembly includes a sensor shield which may be configured as a passive protective mechanism covering a surface of the sensor membrane.

In some implementations, the shield (for example, the passive protective mechanism) covering the surface of the sensor membrane includes a barrier covering the surface of the sensor membrane. In certain implementations, the shield (for example, the barrier) covering the surface of the sensor membrane includes a protective layer deposited on the surface of the sensor membrane. In some implementations, the sensor membrane faces toward a distal end of the blood pump assembly and the protective layer deposited on the surface of the sensor membrane is deposited on the surface of the sensor membrane facing toward the distal end of the blood pump assembly. In certain implementations, the protective layer has a thickness approximately equal to 0.03 mm or greater. In some implementations, the protective layer has a thickness approximately equal to 0.13 mm or greater. In certain implementations, the protective layer includes a material capable of being deposited as a gel and hardening. In some implementations, the protective layer includes a material capable of preventing the sensor membrane from being dissolved by a chemical reaction with blood. In certain implementations, the protective layer includes silicone.

In another aspect, a blood pump assembly includes a drive unit, an impeller blade, a blood pump housing component, a cannula assembly, and a sensor. The cannula assembly is coupled to the blood pump housing component. The blood pump housing component includes a peripheral wall extending about a rotational axis of the impeller blade. The impeller blade is rotatably coupled to the drive unit. The sensor is coupled to the peripheral wall of the blood pump housing component. The sensor includes a sensor membrane configured to deflect in response to a change in a blood parameter. The membrane is coupled to a transmission fiber. The blood pump assembly includes a sensor shield which may be configured as one or more active protective mechanisms for the sensor membrane.

In some implementations, the shield (for example, the one or more active protective mechanisms) includes a mechanism for washing the sensor membrane, for example, a mechanism for washing the sensor membrane with blood. In some implementations, the mechanism for washing the sensor membrane includes one or more components such as a blood aperture extending through the peripheral wall of the blood pump housing component and positioned distal relative to the sensor membrane. In certain implementations, the peripheral wall of the blood pump housing component includes a recess positioned distal relative to the sensor membrane. In some implementations, the recess is wider than the sensor. In certain implementations, the blood aperture is positioned in the recess. In some implementations, the blood aperture permits blood flowing through the cannula assembly and into the blood pump housing component to exit the blood pump housing component and wash the sensor membrane.

In some implementations, the peripheral wall of the blood pump housing component includes one or more blood exhaust windows. In certain implementations, the peripheral wall of the blood pump housing component includes a transmission fiber bed recessed within the peripheral wall of the blood pump housing component, the transmission fiber of the sensor positioned in the transmission fiber bed. The transmission fiber is used to transmit signals sensed by the sensor to a processor for detecting the blood parameter. In some implementations, the sensor includes a glass ring positioned about the transmission fiber.

In certain implementations, the sensor membrane has a thickness of 2 microns or less. In some implementations, the sensor membrane has a thickness of 1.3 microns or less. In certain implementations, the sensor is positioned in a sensor bed in the peripheral wall of the blood pump housing component. In some implementations, the blood pump housing component includes a plurality of struts extending between the blood exhaust windows. The transmission fiber bed may be positioned in a strut of the plurality of struts of the blood pump housing component. In some implementations, the transmission fiber is coupled to the strut of the plurality of struts by an epoxy. The impeller blade may be positioned at least in part in the blood pump housing component. In some implementations, the blood pump housing component is coupled to the drive unit at a first end and the blood pump housing component is coupled to the cannula assembly at a second end opposite the first end. In certain implementations, the cannula assembly includes a blood inflow cage. In some implementations, the blood inflow cage includes a plurality of inlet openings. In certain implementations, a flexible atraumatic extension (for example, a pigtail) is coupled to the blood inflow cage.

In another aspect, a method of manufacturing a blood pump assembly includes coupling a sensor to a peripheral wall of a blood pump housing component, rotatably coupling an impeller blade to a drive unit such that the peripheral wall of the blood pump housing component extends about a rotational axis of the impeller blade, and coupling a cannula assembly to the blood pump housing component. The sensor includes a sensor membrane configured to deflect in response to a change in a blood parameter. The sensor membrane is coupled to a transmission fiber. The sensor may include a sensor visor overhanging the sensor membrane.

In some implementations, the method further includes positioning a sensor visor in a visor notch of a barrier bump protruding from the peripheral wall of the blood pump housing component. In certain implementations, coupling the sensor to the peripheral wall of the blood pump housing component includes affixing (for example, by an epoxy) the sensor to the peripheral wall of the blood pump housing component. In some implementations, coupling the sensor to the peripheral wall of the blood pump housing component includes positioning the sensor into a blood recess in the peripheral wall of the blood pump housing component. In certain implementations, the blood pump housing component includes a plurality of blood exhaust windows and a plurality of struts extending between the blood exhaust windows, and the blood recess is positioned in a strut of the plurality of struts in the blood pump housing component. In some implementations, the method further includes coupling a blood inflow cage to the cannula assembly. In certain implementations, the method further includes coupling a flexible atraumatic extension to the blood inflow cage. In some implementations, a protective layer is deposited over a surface of the sensor membrane. In certain implementations, a protective layer is deposited over a surface of the sensor membrane and the sensor membrane is recessed further below the sensor visor by a distance approximately equal to the thickness of the protective layer.

The sensor detects one or more disturbances or properties of the blood (for example, a deflection caused by a pressure that is used to determine a blood parameter signal). In some implementations, the sensor is a pressure sensor or flow rate sensor. In certain implementations, the sensor transmits its sensed signals optically. In some implementations, the transmission fiber is an optical fiber. In certain implementations, the drive unit is driven by an external motor.

In another aspect, a method of detecting blood pressure includes pumping blood through a cannula assembly coupled to a blood pump housing component and detecting a blood pressure of the blood pumped using an optical pressure sensor coupled to the peripheral wall of the blood pump housing component. The blood is pumped by an impeller blade positioned at least in part in the blood pump housing component. The impeller blade is rotated by a drive unit coupled to the impeller blade. The blood pump housing component includes a peripheral wall extending about a rotational axis of the impeller blade. The optical pressure sensor includes a sensor membrane configured to deflect in response to a change in pressure on the sensor membrane. The sensor membrane is coupled to an optical fiber. The optical pressure sensor includes a sensor visor overhanging the sensor membrane.

In some implementations, pumping blood includes pumping blood through one or more blood exhaust windows in the blood pump housing component. In certain implementations, the method further includes washing the sensor membrane using blood flow through a blood aperture extending through the peripheral wall of the blood pump housing component. The blood aperture is positioned in a blood recess positioned in front of the sensor membrane of the optical pressure sensor. In some implementations, the peripheral wall of the blood pump housing component includes a barrier bump protruding from the peripheral wall of the blood pump housing component. The barrier bump is positioned in front of the blood recess, such that the blood recess is between the barrier bump and the sensor membrane. In certain implementations, the method further includes deflecting the blood flowing through the blood aperture using a sensor visor extending from the optical pressure sensor over the sensor membrane and into a visor notch in the barrier bump. In some implementations, the sensor membrane includes a glass material. In certain implementations, the sensor membrane faces toward a distal end of the pump. In some implementations, the sensor membrane is less than 2 microns thick. In some implementations, a protective layer is deposited over a surface of the sensor membrane. In certain implementations, a protective layer is deposited over a surface of the sensor membrane and the sensor membrane is recessed further below the sensor visor by a distance approximately equal to the thickness of the protective layer.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. Moreover, certain concepts may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the blood pump assemblies, sensors, methods of manufacturing blood pump assemblies, and methods for detecting blood parameters such as pressure or flow contemplated herein, certain illustrative embodiments will be described. Although the embodiments and features described herein are specifically described for use in connection with blood pump assemblies that may be introduced percutaneously during a cardiac procedure through the vascular system, it will be understood that all the components and other features outlined below may be combined with one another in any suitable manner and may be adapted and applied to other types of cardiac therapy and cardiac therapy devices.

The systems, methods, and devices described herein provide a blood pump assembly including a sensor and a shield that protects the sensor from physical damage. The sensor may include a sensor membrane, which may be fragile. The shield can enable the blood pump assembly and sensor to traverse torturous and/or calcified anatomy of the vascular system and remain operable, such as by protecting the sensor membrane. The shield may include one or more passive protective mechanisms, active protective mechanisms, or a combination of both. Passive protective mechanisms may include one or more barriers which protect the sensor membrane. As an example, a sensor visor may prevent soft obstructions, such as valve leaves on a blood pump introducer, from contacting and damaging the sensor membrane. A barrier bump is another example of a passive protective mechanism and can be positioned distal relative to the sensor membrane. The barrier bump may deflect calcification or other obstacles within the vascular system and/or prevent the sensor membrane from being damaged when the pump changes direction during delivery of the pump through the vasculature and into the heart. The shield may also include an additional protective layer (for example, a layer of silicone) covering the sensor membrane. As an example, this protective layer may prevent the sensor membrane from being dissolved by chemical reactions with a patient's blood without significantly influencing or interfering with accurate detection of pressure. A mechanism for washing the sensor membrane is an example of an active protective mechanism for the sensor. For example, a blood aperture can be positioned adjacent to the sensor membrane and blood flowing through the aperture may wash the front end of the sensor membrane to prevent buildup or clotting of blood on the surface of the sensor membrane.

Figure 1:
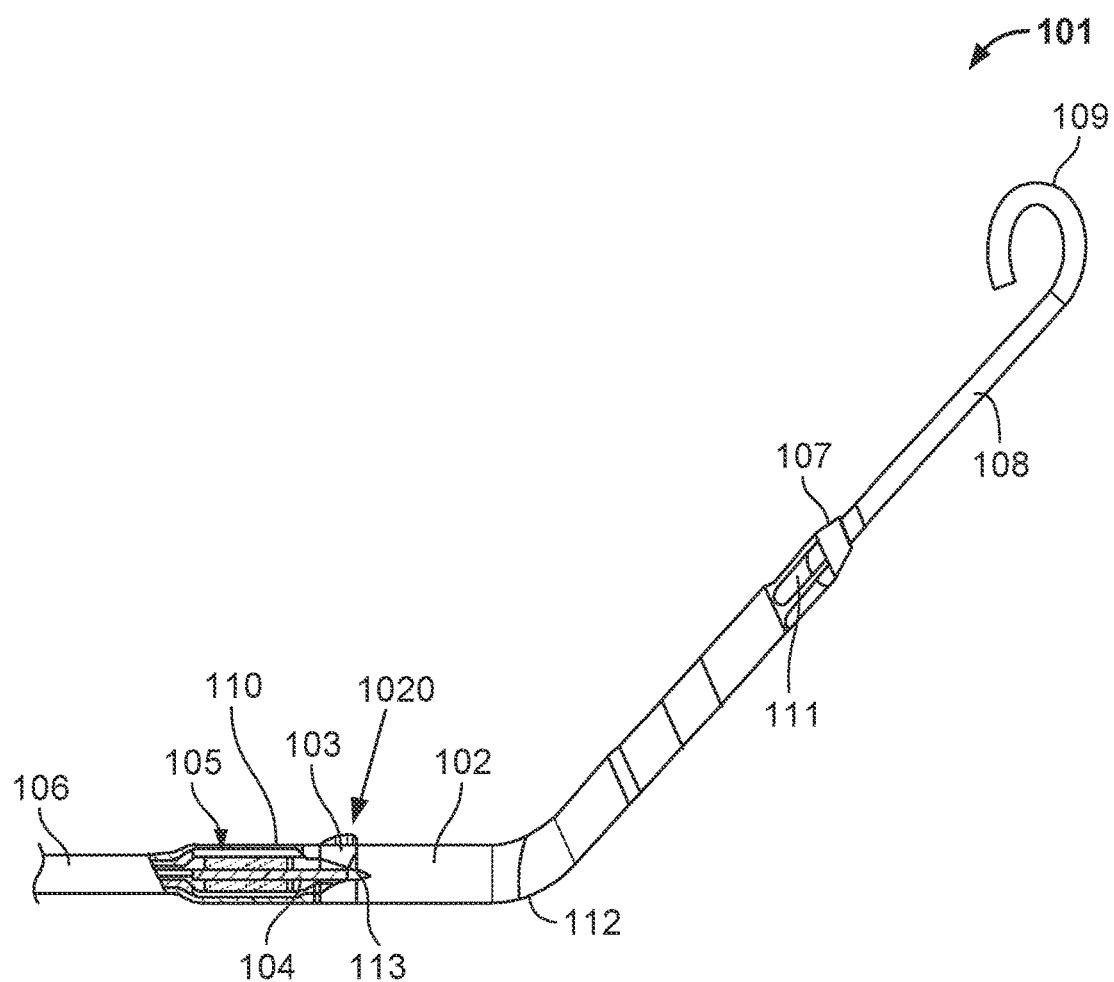
FIG. 1 is a side view of an exemplary catheter-based blood pump assembly having a sensor and exemplary shielding features for protecting the sensor.
Figure 2:
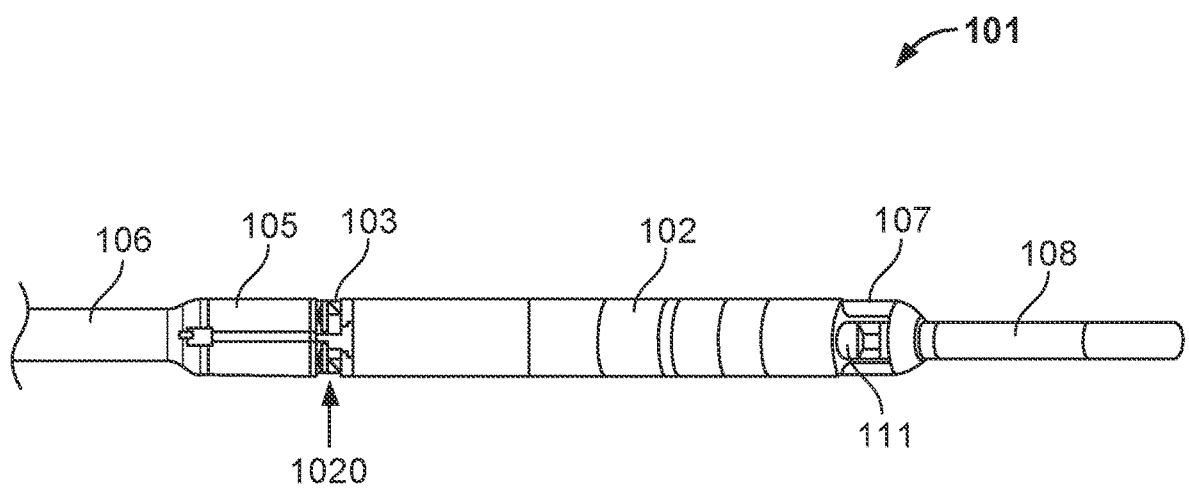
FIG. 2 is a top view of the blood pump assembly of FIG. 1.
Figure 3:
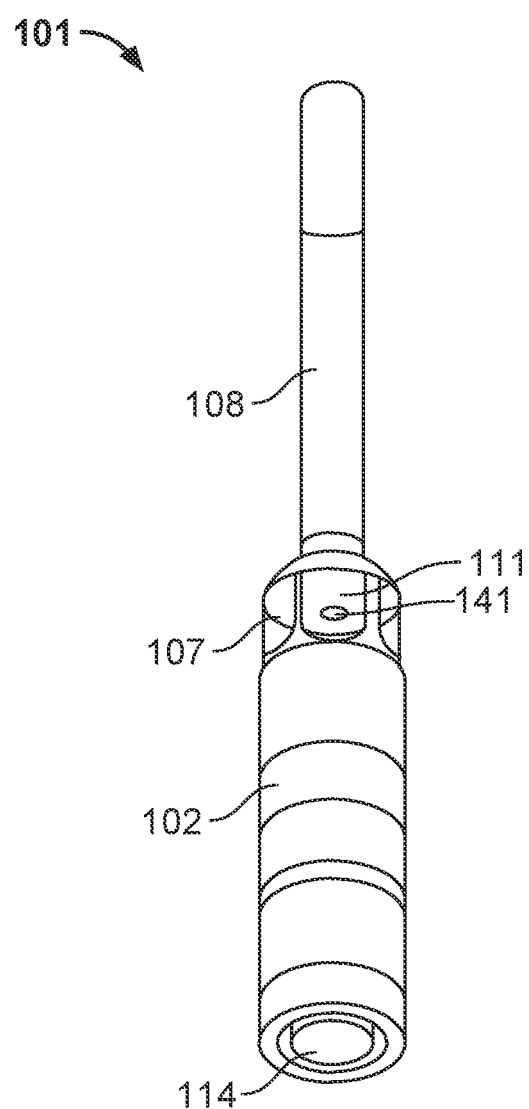
FIG. 3 is a partial top view of the blood pump assembly of FIG. 1.

FIG. 1 is a side view of an exemplary catheter-based blood pump assembly 101 having a sensor 1020 and exemplary shielding features for protecting the sensor 1020. FIG. 2 is a top view of the blood pump assembly 101, and FIG. 3 is a partial top view of the blood pump assembly 101. As shown, the blood pump assembly 101 includes a cannula assembly 102, the sensor 1020, a catheter shaft 106, a flexible atraumatic extension (for example, a pigtail) 108, a blood pump motor 110, a blood pump motor housing 105, a blood pump housing component 103, a drive shaft 104, an impeller hub 113, a blood inflow cage 107, and a guidewire hole 141. The pigtail extension 108 includes a curved portion 109. The blood inflow cage 107 includes one or more input ports 111. The interior of the blood pump housing component 103 is contiguous with the interior of the cannula assembly 102. The cannula assembly 102 is coupled to the blood pump housing component 103 and the blood pump housing component 103 is coupled to the blood pump motor housing 105. The blood pump housing component has a substantially cylindrical and elongate shape. The blood pump motor 110 is housed in the blood pump motor housing 105. As an alternative, in certain other implementations, the blood pump motor 110 has an integrated housing such that the outer layer of the blood pump motor 110 is the blood pump housing 105.

As used herein, "distal" means in the direction in which the blood pump assembly is inserted into a blood vessel, and "proximal" is opposite the distal direction. For example, in FIG. 1, the extension 108 is distal to the sensor 1020 and the catheter shaft 106 is proximal to the sensor 1020.

The cannula assembly 102 includes the blood inflow cage 107, which is positioned toward the distal end of the cannula assembly 102 opposite from the proximal blood pump housing component 103. The catheter shaft 106 extends from the blood pump motor housing 105 at the proximal end of the blood pump assembly 101. The flexible atraumatic extension (for example, pigtail) 108 extends distally from the blood inflow cage 107 at the distal end of the blood pump assembly 101. The blood pump assembly 101 may be configured as a pump for the left side of the heart or for the right side of the heart.

The sensor 1020 may sense blood pressure, blood flow rate, and/or other parameters. The sensor 1020 transmits its sensed signals to a transducer system to convert the signal into the desired physical or medical variable including signal conditioning and data acquisition system for linearization and calibration of the parameter. For example, the sensor 1020 may be an optical pressure sensor that transmits optical signals or an electrical sensor.

The cannula assembly 102 provides at least one central lumen 114 configured to facilitate blood flow therein. The cannula assembly 102 includes a bend 112. In some embodiments, the bend 112 is 45°. One skilled in the art will appreciate that other configurations for the cannula assembly 102 are possible. In certain implementations being designed for use in the right heart, the cannula assembly 102 can have one or more bends and may have different and/or multiple bend radii to adapt to the needs of passage and final position of the cannula assembly 102. In certain embodiments, the cannula assembly 102 need not have a bend. In certain embodiments, the diameter of the cannula assembly 102 is about equal to or greater than 9 Fr (3 mm). For example, the diameter of the cannula assembly 102 may be 9 Fr (3 mm), 10 Fr (3.33 mm), 11 Fr (3.67 mm), 12 Fr (4 mm), >12 Fr, or any other suitable diameter. In some embodiments, the diameter of the cannula assembly 102 is about equal to or less than 9 Fr (3 mm). For example, the diameter of the cannula assembly 102 may be 8 Fr (2.67 mm), 7 Fr (2.33 mm), 6 Fr (2 mm), <6 Fr, or any other suitable diameter.

The drive shaft 104 transfers torque from the blood pump motor 110 to the impeller hub 113. For example, a proximal end portion (not shown) of the drive shaft 104 can be coupled to a rotor of the blood pump motor 110 and a distal end (not shown) of the drive shaft 104 can be coupled to the impeller hub 113. In some embodiments, a flexible drive cable, a magnetic clutch, and/or magnetic drive components transfer torque from the blood pump motor 110 to the impeller hub 113. In certain embodiments, the blood pump motor 110 can be positioned external to the patient and configured to rotate the rotor of the blood pump motor 110 when the blood pump assembly 101 is positioned in the patient's heart, and a drive shaft or drive cable can be coupled to the rotor of the blood pump motor 110. In such embodiments, the blood pump motor 110 is absent from the blood pump motor housing 105. For those embodiments, the blood pump motor housing 105 is modified to reduce rigid diameter and/or length of the pump.

The cannula assembly 102 also includes a blood inflow cage 107 positioned toward an opposite end of the cannula assembly 102 than the blood pump housing component 103. The blood inflow cage 107 includes one or more input ports 111. The blood pump assembly 101 is configured such that actuation of the blood pump motor 110 and the drive shaft 104 rotates the impeller hub 113 (which may include an impeller blade not shown in FIGS. 1-3) and draws blood or other fluid into the blood inflow cage 107 (or blood inlet manifold) through the one or more input ports 111. The blood received through the blood inflow cage 107 travels through the cannula assembly 102 to the blood pump housing component 103. The blood entering the blood pump housing component 103 is exhausted from the blood pump housing component 103 through windows or blood exhaust apertures (not shown in figure) in an outflow cage at a proximal end of the blood pump housing component 103. In some embodiments, the flow direction can be opposite as that of the devices illustrated herein. In such embodiments, inflow of blood occurs at the side of the cannula assembly 102 which is connected to the blood pump housing component 103 and outflow of blood occurs at the opposite side of the cannula assembly 102. When placed in a patient, the blood pump assembly 101 can pump blood from the left ventricle (via the blood inflow cage 107) to the aorta (via the blood exhaust apertures). The blood pump assembly 101 includes a catheter shaft 106 extending from the blood pump motor housing 105 at the proximal end of the blood pump assembly 101. The catheter shaft 106 houses electrical connector cables providing power and control signals to the blood pump motor 110 and receiving information from one or more sensors such as the sensor 1020, discussed further herein in accordance with particular embodiments. In some embodiments, the catheter shaft 106 includes one or more lumens to facilitate receipt of purge fluid and to be used as a conduit for a transmission fiber. In some embodiments, the interior of one or more lumens of the catheter shaft 106 is coated with a polytetrafluoroethylene (PTFE) lining, e.g., Teflon, over at least a portion of the one or more lumens' length. Because the PTFE lining has a low coefficient of friction, the transmission fiber moves more freely through the one or more lumens, and is easier to insert or retract as needed.

The blood pump assembly 101 includes a flexible atraumatic extension 108 (for example, a pigtail) extending from the blood inflow cage 107 at a distal end of the blood pump assembly 101. The extension 108 includes a curved portion 109. The extension 108 assists with stabilizing the blood pump assembly 101 in the correct position, for example in the left ventricle. In certain embodiments, the extension 108 is configurable from a straight configuration to a partially curved configuration. Accordingly, the extension 108 may be composed, at least in part, of a flexible material.

Figure 4:
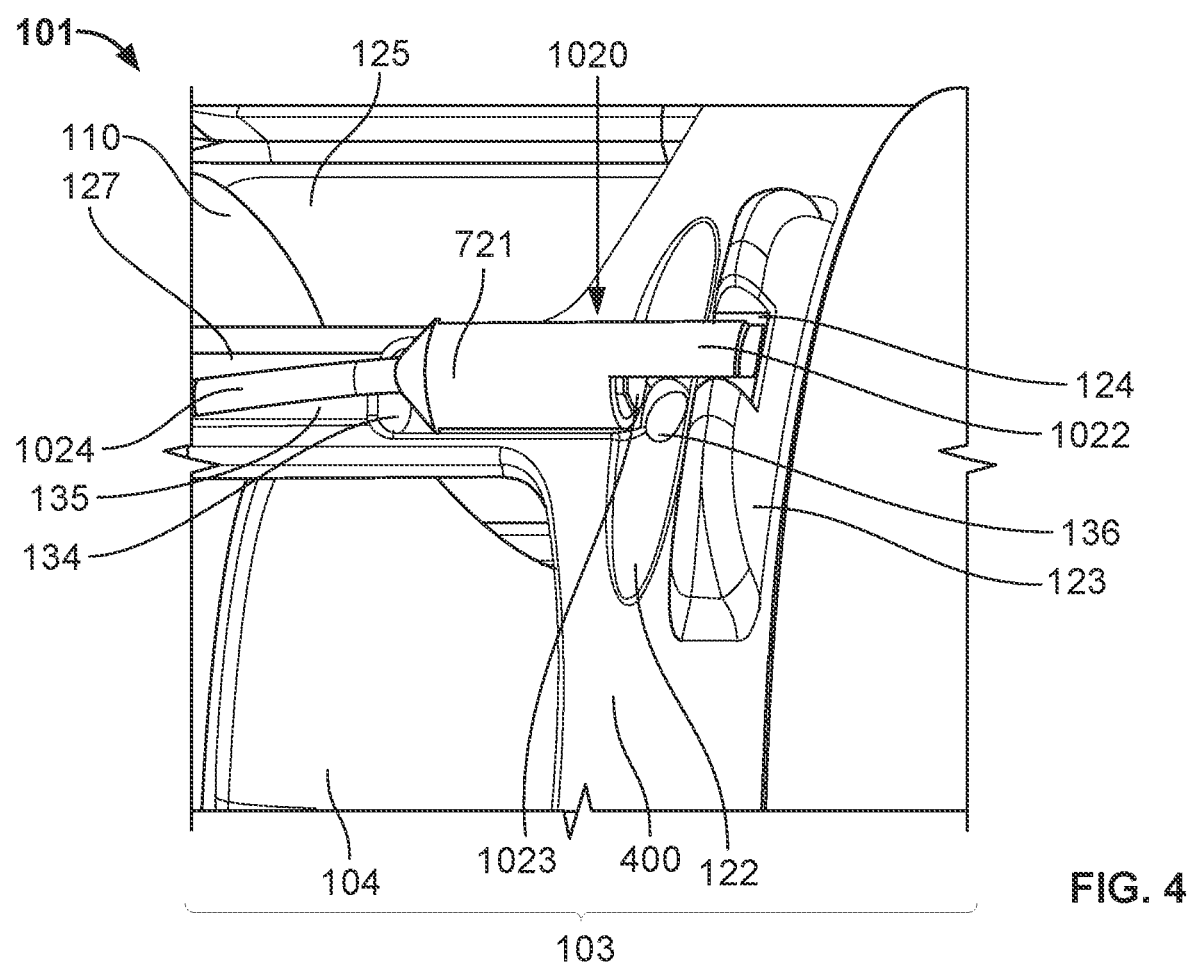
FIG. 4 is a magnified perspective view of the sensor mounted on an outflow cage of the blood pump assembly of FIG. 1.
Figure 5:
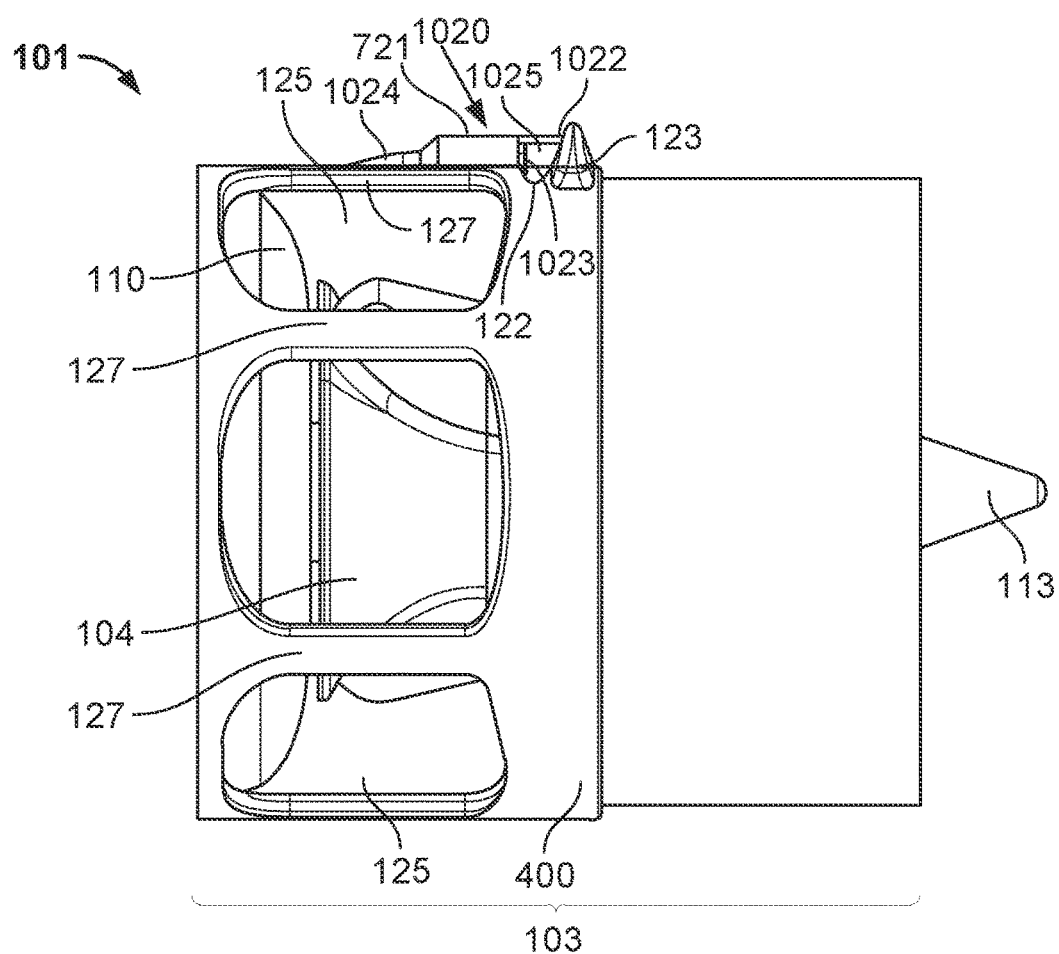
FIG. 5 is a magnified side view of the sensor and outflow cage of FIG. 4.
Figure 6:
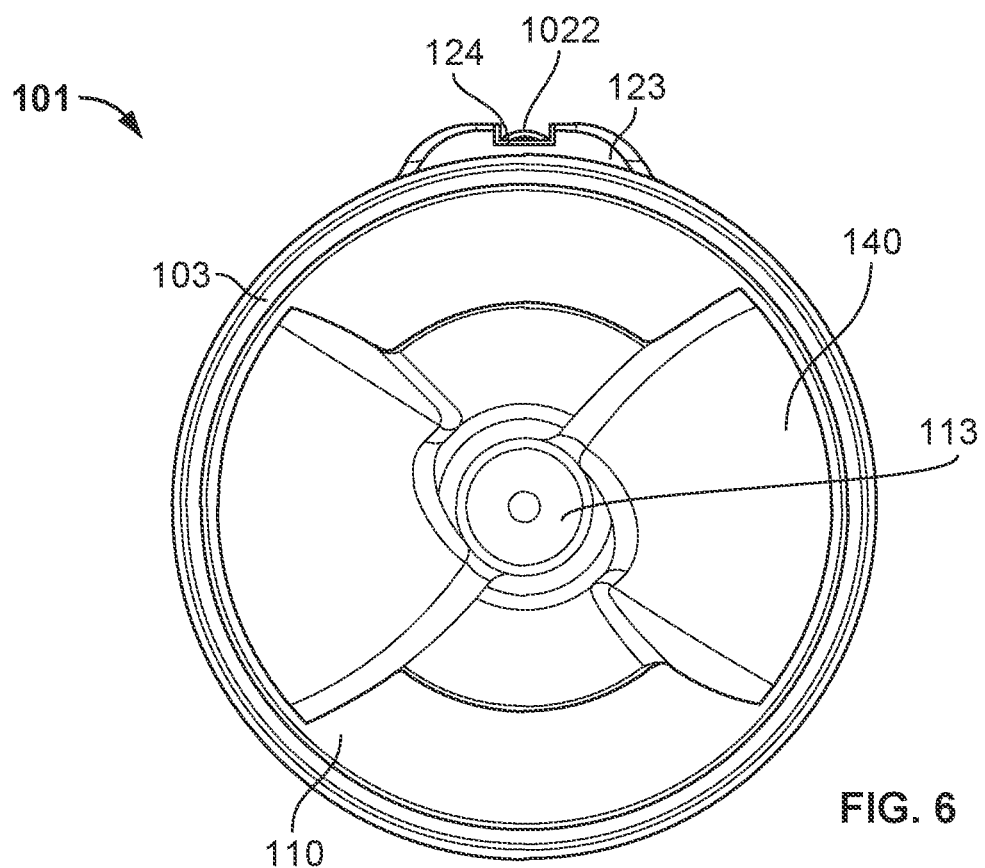
FIG. 6 is a magnified end view of the blood pump assembly of FIG. 4 showing the impeller hub, impeller blade, and exemplary shielding features for protecting the sensor.
Figure 7:
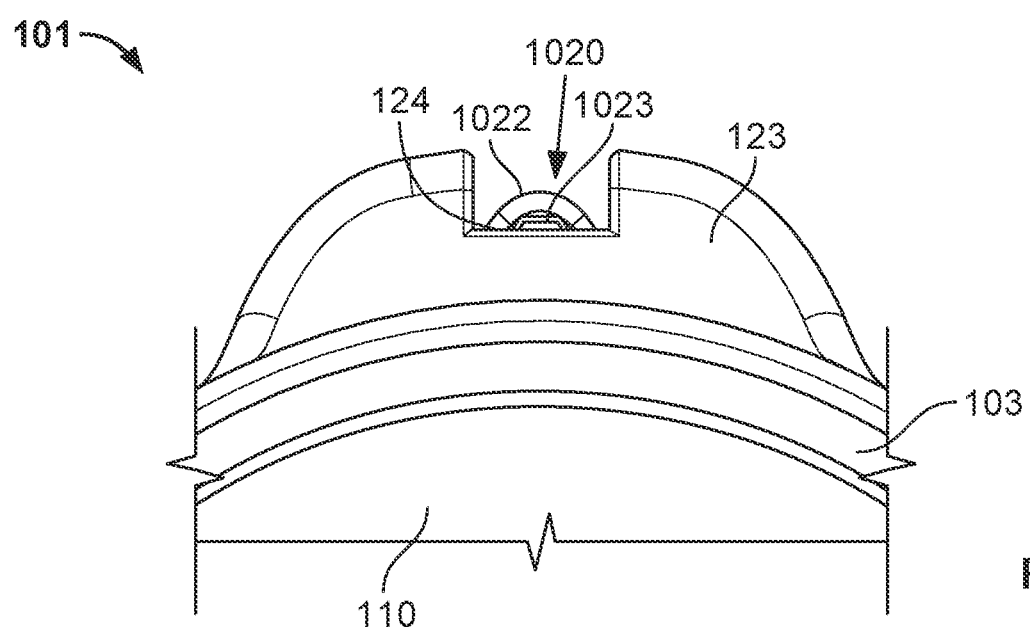
FIG. 7 is a magnified end view of the sensor and shielding features of the blood pump assembly of FIG. 4.
Figure 8:
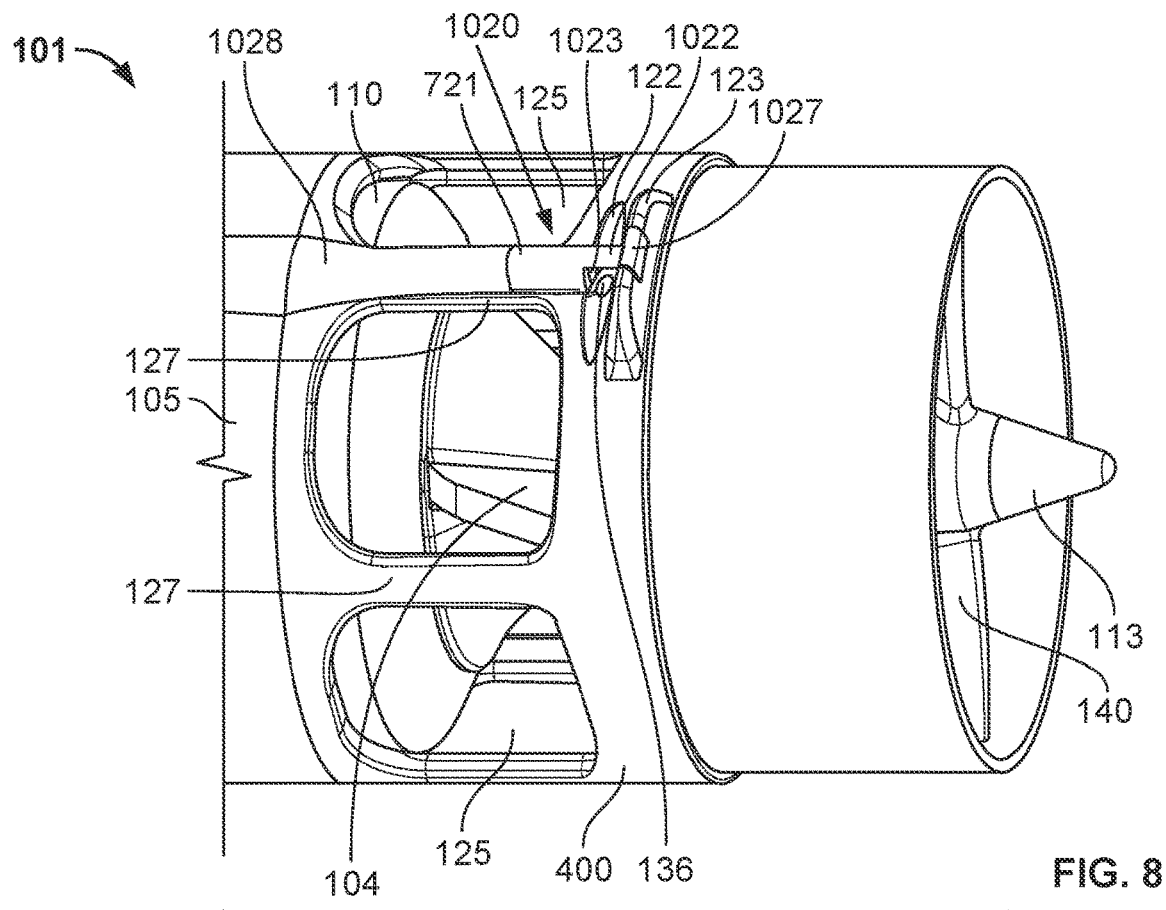
FIG. 8 is a perspective view of the blood pump assembly of FIG. 4 showing a cap and cover which provide smooth transitions between the outflow cage and the shielding features.

FIGS. 4-8 show various views of the sensor 1020 mounted on the blood pump assembly 101 of FIG. 1. FIG. 4 is a magnified perspective view of the sensor 1020 mounted on an outflow cage 400 of the blood pump assembly 101 of FIG. 1. FIG. 5 is a magnified side view of the sensor 1020 and the outflow cage 400 of FIG. 4. FIG. 6 is a magnified end view of the blood pump assembly 101 of FIG. 4 showing the impeller hub 113, impeller blade 140, and exemplary shielding features for protecting the sensor 1020. FIG. 7 is a magnified end view of the sensor 1020 and shielding features of the blood pump assembly 101 of FIG. 4. FIG. 8 is a perspective view of the blood pump assembly 101 of FIG. 4 showing a cap and cover which provide smooth transitions between the outflow cage 400 and the shielding features. For clarity, the cannula assembly 102 is omitted from FIGS. 4-8.

As shown, the blood pump assembly 101 can include a shield. The shield may include a sensor visor, a barrier bump, an additional protective layer (for example, a silicone layer), and/or a blood aperture. In FIGS. 4-8, for example, the shield includes a sensor visor 1022, a barrier bump 123, and a blood aperture 136. In FIGS. 4-8, the blood pump assembly 101 further includes a plurality of struts 127, one or more output ports 125, a sensor bed 134, a transmission fiber 1024, a recess 122, an impeller blade 140, and a transmission fiber bed 135. The blood pump housing component 103 includes the outflow cage 400. The sensor 1020 includes a sensor head 721 and a sensor membrane 1023. In embodiments having both a barrier bump 123 and a sensor visor 1022, the barrier bump 123 may include a mechanism for connecting to the sensor visor 1022. For example, in FIGS. 4-8, the barrier bump 123 includes a visor notch 124 that receives and holds a portion of the sensor visor 1022 in a fixed position. The sensor 1020 is attached to the outflow cage 400 of the blood pump housing component 103. For example, in FIGS. 4-7, the sensor 1020 is coupled distal to one of the plurality of struts 127 of the outflow cage 400 of the blood pump housing component 103 and sits in the sensor bed 134. Preferably, the sensor 1020 is not positioned on one of the plurality of struts 127. For example, in some embodiments, the sensor 1020 is positioned on a portion of the outflow cage 400 distal to the struts 127 (e.g., 0.1 mm distal, 0.5 mm distal, 1 mm distal, 2 mm distal, 5 mm distal, 1 cm distal or any other suitable distance). Alternatively, the sensor 1020 can be positioned on the blood inflow cage (e.g., blood inflow cage 107) or on the cannula (e.g., cannula assembly 102).

The sensor membrane 1023 of the sensor 1020 is configured to deflect in response to changes in blood parameters, for example, changes in pressure, flow rate, fluid composition, and/or viscosity. The sensor membrane 1023 is preferably thin. In some embodiments, the sensor membrane 1023 is less than two microns thick. In some embodiments, the sensor membrane 1023 is composed of a fragile glass material such as silicon, silicon dioxide, or silicon nitride. Deflections of the sensor membrane 1023 are used to measure changes in blood parameters (for example, blood pressure) at the blood pump assembly 101. Due to the bend radius constraints of the transmission fiber 1024, the sensor membrane 1023 points forward towards the distal end of the blood pump assembly 101. Deflections of the sensor membrane 1023 are sensed by the sensor head 721 and transmitted to the transmission fiber 1024. The transmission fiber 1024 transmits the sensor's sensed signals to an optical bench for signal evaluation. The transmission fiber 1024 can extend across various locations on the blood pump assembly 101 depending on the location of the sensor 1020 relative to other components of the blood pump assembly 101. In FIG. 4, the transmission fiber 1024 extends along one of the plurality of struts 127 of the blood pump housing component 103, along the blood pump motor housing 105, and through the catheter shaft 106 (not shown). In some embodiments, the transmission fiber 1024 is coated with a protective coating, such as a polymer (for example, polyimide). The transmission fiber 1024 is attached to the blood pump housing component 103. In FIG. 4, for example, the transmission fiber 1024 is positioned in the transmission fiber bed 135 recessed in the outflow cage 400 of the blood pump housing component 103. The measured blood parameters (for example, pressure) and changes in such parameters provide information regarding operation of the blood pump assembly 101, the location of the blood pump assembly 101 (for example, in pressure sensor embodiments, pressure differences are associated with various locations in the heart), and vital signs of the patient in response to placement and operation of the blood pump assembly 101.

In embodiments with sensors that transmit sensed signals optically, the transmission fiber 1024 is an optical fiber and the transmission fiber 1024 extends to a light source. In such embodiments, the reflection of light or resonant frequencies (e.g., in embodiments using the sensing principle of a Fabry-Perot resonator) within the sensor head 721 changes in response to changes in the position of the sensor membrane 1023 under deflection in response to changes in blood parameters. Changes in the reflection of light or resonant frequencies are transmitted by the transmission fiber 1024 from the sensor head 721 to an optical bench (or other suitable components configured to convert optically modulated pressure signal into electrically calibrated or digital data which can be stored and/or analyzed using software) for signal evaluation. The optical bench may be remote from the blood pump housing component 103, for example located outside of the body in a console or in a connector. In embodiments with sensors that sense pressure, the movement of the sensor membrane 1023 in response to changes in pressure on the surface of the sensor membrane 1023 is transmitted by the transmission fiber 1024 to an optical bench or transducer for pressure determination. The sensors may transmit sensed pressure signals optically, as discussed above.

The barrier bump 123 is positioned in front of/distal to the sensor membrane 1023 to protect the sensor membrane 1023. The barrier bump 123 protrudes from the outflow cage 400 of the blood pump housing component 103. In some embodiments, the barrier bump 123 is composed of the same material as the blood pump housing component 103, such as stainless steel. The barrier bump 123 may be electropolished, mechanically polished, or otherwise processed in such a way that it provides smooth surfaces that minimize thrombosis and blood flow shear stress. In particular, it is preferred that all surfaces of the barrier bump 123 which will be in contact with blood be smooth so as to minimize thrombosis and blood flow shear stress. The sensor 1020 may include various other protective features. In embodiments having both a barrier bump 123 and a sensor visor 1022, such as the embodiment shown in FIGS. 4-8, the barrier bump 123 may include a visor notch 124 configured to receive and hold the sensor visor 1022 in a fixed position. Other mechanisms could be employed for connecting the sensor visor 1022 to the barrier bump 123, such as adhesive (for example, epoxy), welding, etc.

As shown, the sensor visor 1022 can be a shroud that extends over the sensor membrane 1023. In embodiments having both a barrier bump 123 and a sensor visor 1022, such as the embodiment shown in FIGS. 4-8, the sensor visor 1022 may extend to the visor notch 124 in the barrier bump 123. The sensor visor 1022 helps to direct or deflect flow of blood exiting the blood pump housing component 103 through the blood aperture 136. The sensor visor 1022 deflects blood to the sensor membrane 1023 of the sensor 1020 and out to the sides through the recess 122. In some embodiments, the sensor visor 1022 is composed of stainless steel. The sensor visor 1022 may have a curved geometry. The sensor visor 1022 preferably has smooth surfaces for some or all of its surfaces in contact with blood so as to prevent thrombosis. The sensor visor 1022 may be composed, at least in part, of a biocompatible material and/or may have a biocompatible material coating.

As discussed herein, a blood pump assembly 101 may be introduced percutaneously during a cardiac procedure through the vascular system. For example, the blood pump assembly 101 can be inserted by a catheterization procedure through the femoral artery, into the ascending aorta, across the valve, and into the left ventricle such that the blood pump assembly 101 can provide support to the left side of the heart. As noted, introducing the blood pump assembly 101 through an introducer unit into the vascular system may include traversing torturous directional changes and a calcified anatomy in the vascular system. The sensor 1020, and in particular the sensor membrane 1023, may be composed of sensitive or brittle components that may be easily damaged by the torturous and calcified anatomy of the vascular system. The barrier bump 123 and the sensor visor 1022 permit the sensor 1020 to traverse the torturous and calcified anatomy of the vascular system and remain operable. For example, the barrier bump 123 may protect the sensor membrane 1023 by deflecting upcoming obstacles presented by calcification within the vascular system or changes in direction of the sensor 1020. As another example, the sensor visor 1022 may protect the sensor membrane 1023 by preventing soft obstructions, such as valve leaves on a blood pump introducer, from contacting and damaging the sensor membrane 1023. In embodiments having both a barrier bump 123 and a sensor visor 1022, such as the embodiment shown in FIGS. 4-8, obstacles deflected by the barrier bump 123 may ride over the sensor visor 1022, thereby preventing the obstacles from contacting and/or damaging the sensor membrane 1023.

The sensor membrane 1023 is positioned in the recess 122 and positioned adjacent to the blood aperture 136. The recess 122 is where blood flowing from cannula assembly 102 is introduced to and directly or indirectly interacts with the sensor membrane 1023 so that the fluid pressure may be determined. In FIGS. 4-8, blood can directly interact with the sensor membrane 1023. In embodiments in which there are one or more protective layers deposited over the sensor membrane 1023 (as discussed below in relation to FIGS. 11-12), blood indirectly interacts with the sensor membrane 1023. The recess 122 is configured to be wider than the sensor 1020 so that the blood can easily flow away, for example laterally, from the sensor 1020, allowing for pressure equivalence with the pressure on the outside of the outflow cage 400 of the blood pump housing component 103. In some embodiments, the width of the recess 122 is configured to be about equal to or less than the width of the sensor 1020.

The blood aperture 136 can allow blood to flow toward the sensor membrane 1023 and then exit the blood pump housing component 103. In the illustrated embodiment, the blood aperture 136 is positioned distal to the sensor membrane 1023 and the blood aperture 136 is in the recess 122. The blood aperture 136 permits blood flowing through the cannula assembly 102 to wash the front end of the sensor membrane 1023 to prevent buildup or clotting of blood on the surface of the sensor membrane 1023. As shown, the blood aperture 136 extends from the interior of the blood pump housing component 103 into the recess 122. The blood aperture 136 also permits blood flowing from the cannula assembly 102 into the blood pump housing component 103 to exit the blood pump housing component 103 in a manner similar to the way that blood exits the blood pump housing component 103 through the one or more output ports 125. Blood exiting the blood pump housing component 103 through the blood aperture 136 flows past the sensor membrane 1023 in the recess 122. The blood aperture 136 may be approximately 250 microns in diameter. In some embodiments, the diameter of the blood aperture 136 is greater than 250 microns, for example, 275 microns, 300 microns, 325 microns, 350 microns, >350 microns, or any suitable diameter. In other embodiments, the diameter of the blood aperture 136 is less than 250 microns, for example, 225 microns, 200 microns, 175 microns, 150 microns, 125 microns, 100 microns, <100 microns, or any suitable diameter. In some embodiments the flow can be directed inwards. In certain embodiments, the flow can be bidirectional and blood can enter and exit the blood aperture 136, washing the sensor membrane 1023. The blood aperture 136 preferably has smooth surfaces for some or all of its surfaces in contact with blood so as to prevent thrombosis. In embodiments where the sensor 1020 and the sensor membrane 1023 are positioned more distal than the positioning shown in FIGS. 4-8, the likelihood of clotting of blood increases and the blood aperture 136 becomes more important. In other embodiments in which the sensor 1020 and the sensor membrane 1023 are positioned more proximally than the positioning shown in FIGS. 4-8, it may not be necessary to have a blood aperture 136, and instead the sensor membrane 1023 can be directly open with the blood.

The sensor 1020 can be attached to the outflow cage 400 of the blood pump housing component 103 (or other components of the blood pump assembly 101, such as the inflow cage 107) in various ways. In FIG. 4, the sensor 1020 sits in the sensor bed 134, which is configured to receive the sensor 1020 in a recessed position in the outflow cage 400 of the blood pump housing component 103. The sensor bed 134 extends directly into the recess 122 to provide and facilitate an interface between the sensor membrane 1023 and the blood entering the recess 122 through the blood aperture 136. In some embodiments, the sensor bed 134 includes laser texturing strips to facilitate placement and holding of the sensor 1020 therein. In certain embodiments, the sensor bed 134 includes potting and/or smoothing by the use of epoxy or silicone to smooth structures in and/or around the sensor bed 134.

As shown in FIG. 5, an opening/window 1025 allows blood exiting or entering the blood aperture 136 (shown in FIG. 4) to wash the sensor membrane 1023. The barrier bump 123 is structured to have a height that is greater than the height (e.g. in a direction radially outward from a central longitudinal axis extending through the blood pump assembly 101) of the sensor 1020 to raise the position of any obstacles encountered during insertion of the sensor 1020. The obstacles are then able to rise over and be diverted away from the sensor 1020 and in particular over the sensor membrane 1023. For example, the obstacles can ride along the sensor visor 1022 without contacting the sensor membrane 1023. The sensor 1020 is recessed in the outflow cage 400 of the blood pump housing component 103 distal to one of the plurality of struts 127. Positioning the sensor 1020 more distal on the blood pump housing component 103 than the position shown in FIG. 5 can help with repositioning the blood pump assembly 101. In some embodiments, the sensor 1020 and/or the sensor visor 1022 may be coupled to the outflow cage 400 of the blood pump housing component 103 (or another component of the blood pump assembly 101, such as the inflow cage 107) and the barrier bump 123 with an adhesive, including but not limited to an epoxy, may be welded, or may be coupled together using other fixation techniques known to persons skilled in the art.

The blood pump housing component 103 can house the drive shaft 104 which can be coupled to the blood pump motor 110 to permit axial rotation of the drive shaft 104. The drive shaft 104 is coupled to the impeller hub 113 at a distal end portion of the drive shaft 104. The impeller hub 103 is coupled to the impeller blade 140. The impeller blade 140 draws blood through the cannula assembly 102 to create a highly viscous helical flow of blood, the blood exiting the blood pump housing component 103 through a plurality of blood exhaust windows 125 provided in the sidewall of the outflow cage 400 of the blood pump housing component 103. In some embodiments, the exhaust windows are formed in walls of the cannula assembly 102 instead of or in addition to being formed in the blood pump housing component 103. The impeller blade 140 may be expandable or compressible. The outflow cage 400 includes a plurality of struts 127 positioned around the outflow cage 400. The plurality of struts 127 separate the one or more output ports 125. At least one of the plurality of struts 127 includes the transmission fiber bed 135 for the transmission fiber 1024 and aligns to the sensor bed 134 and the transmission fiber bed 135 (shown in FIG. 4) for housing the sensor 1020 and the transmission fiber 1024, respectively.

In some embodiments, the blood pump assembly 101 includes features providing smooth transitions over certain structures of the blood pump assembly 101. As shown in FIG. 8, a cap 1027 covers the visor notch 124 (not visible in figure) when the sensor visor 1022 is properly positioned. The cap 1027 may include an adhesive, epoxy, weld, or other structure or material that can hold the sensor visor 1022 in place and/or provide a smooth transition across the barrier bump 123. Similarly, the sensor 1020 and/or the transmission fiber 1024 (not visible) are coupled to the outflow cage 400 of the blood pump housing component 103 through a cover 1028, which may include but is not limited to a layer of epoxy providing a smooth transition across the sensor 1020 as well as securing the sensor 1020 and the transmission fiber 1024 in place. One skilled in the art will appreciate that various other features providing smooth transitions over certain structures of the blood pump assembly 101 are possible. Preferably, all surfaces of the blood pump assembly 101 that touch blood are smooth to minimize thrombosis and blood flow shear stress.

Figure 9:
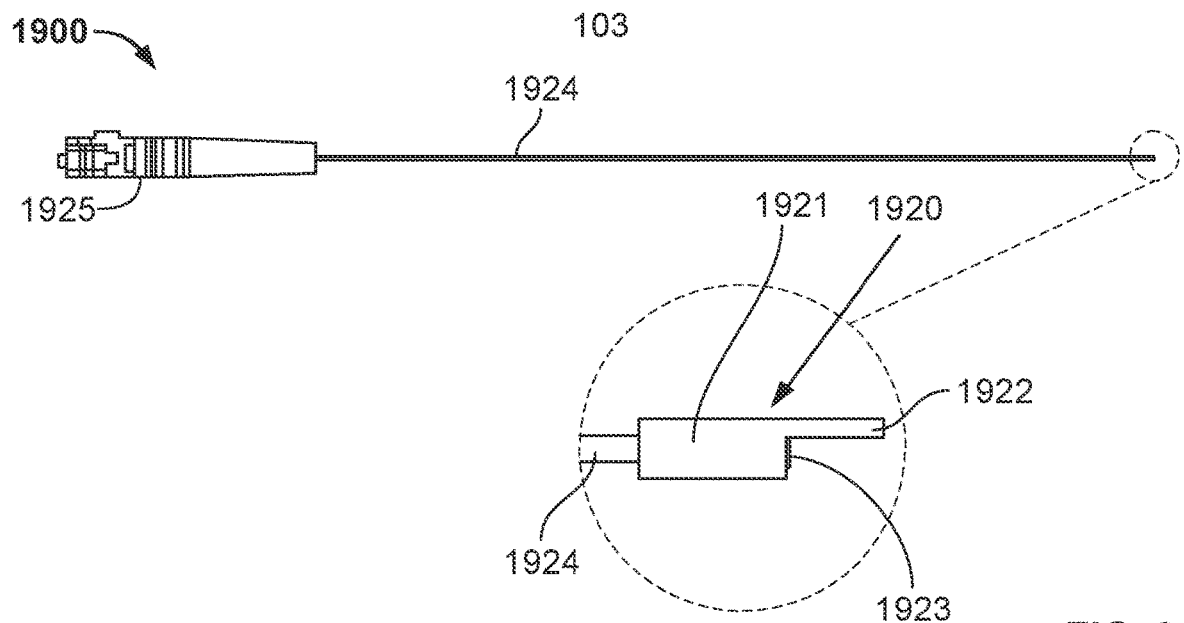
FIG. 9 is a side view of a sensing assembly for a catheter-based blood pump assembly.

FIG. 9 is a side view of a sensing assembly 1900 for a catheter-based blood pump assembly. The sensing assembly 1900 includes a sensor 1920, a sensor visor 1922, a transmission fiber 1924, and a connector 1925. The sensor 1920 includes a sensor head 1921 and a sensor membrane 1923. The sensor head 1921 houses sensing components. The sensor visor 1922 may be composed of a material including but not limited to stainless steel. The transmission fiber 1924 extends from the connector 1925 to the sensor head 1921. In embodiments where the sensing assembly 1900 senses pressure and transmits sensed signals optically, the transmission fiber 1924 optically couples the sensor head 1921, through the connector 1925, to a light source configured to send light to the sensor membrane 1923 and the modulated signal back to the optical bench/transducer. As pressure is applied to the sensor membrane 1923 under the high pressure and/or vacuum caused by the impeller blade (not shown in figure) rotating, the sensor membrane 1923 deflects, causing a change/modulation of the reflected light which is sent back from the sensor head 1921. The change in the light is detected on behalf of the optical bench/transducer and the change in pressure is determined.

Figure 10:
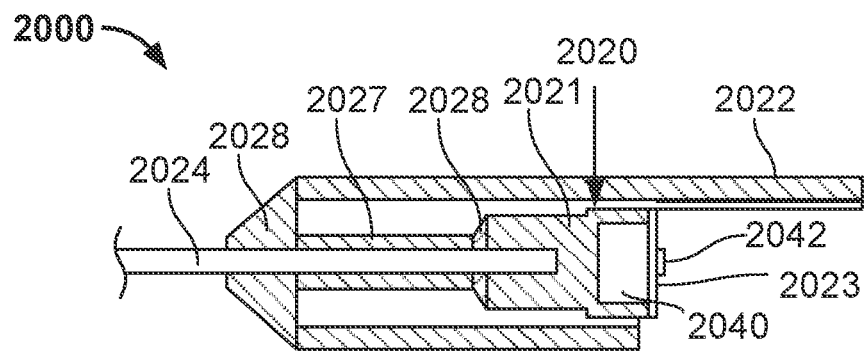
FIG. 10 is a partial side cross-sectional view of a sensing assembly for a catheter-based blood pump assembly.

FIG. 10 is a partial side cross-sectional view of a sensing assembly 2000 for a catheter-based blood pump assembly. The sensing assembly 2000 includes a sensor 2020, a transmission fiber 2024, a jacket 2027, glue 2028, and a sensor visor 2022. The sensor 2020 includes a sensor head 2021, a sensor membrane 2023, and a temperature compensation portion 2042. The sensor head 2021 includes a cavity 2040. The transmission fiber 2024 ends in the proximal portion of the sensor head 2021 to which it is coupled with low loss. The cavity 2040 in combination with the sensor membrane 2023 forms a Fabry-Perot resonator. To allow for the resonant measuring principle, both sides of the cavity 2040 are manufactured to reflect light. As far as detection of the signal has to be made possible, on one side, preferably the transmission fiber 2024 side, partial reflection is realized, and preferably on the sensor membrane 2023 side, full reflection is realized. The temperature compensation portion 2042 is configured to prevent drift in sensed signals due to temperature fluctuations. The temperature compensation portion 2042 is smaller in size than the sensor membrane 2023 and may include silicon dioxide. The jacket 2027 is positioned about the transmission fiber 2024 and may include a glass ring. The transmission fiber 2024 is coupled to the sensor head 2021 by the glue 2028, which may be ultraviolet-curing epoxy. The sensor visor 2022 is configured to extend beyond a distal end of the sensor membrane 2023.

Figure 11:
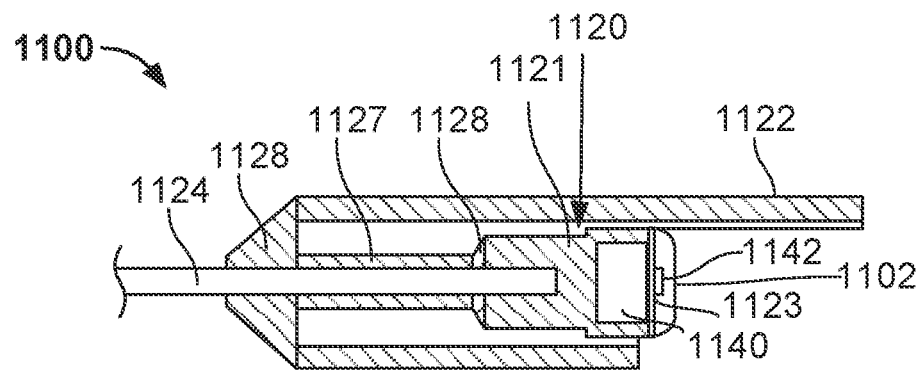
FIG. 11 is a partial side cross-sectional view of another sensing assembly including an additional protective layer covering the sensor membrane.
Figure 12:
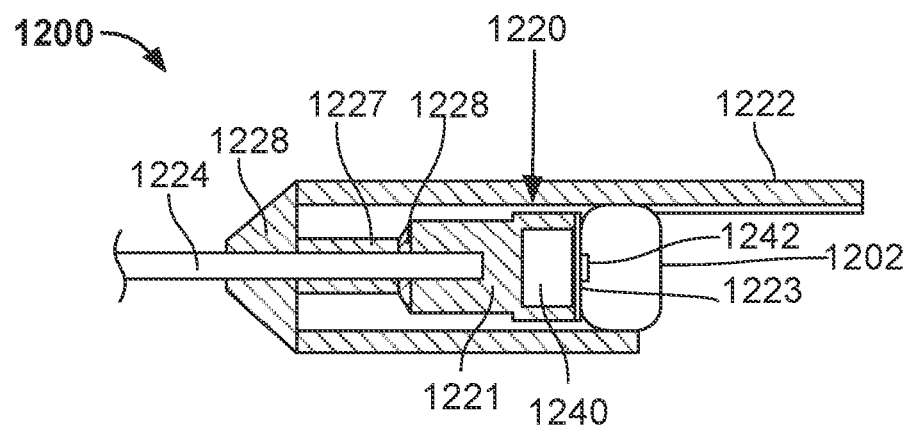
FIG. 12 is a partial side cross-sectional view of another sensing assembly including an additional protective layer covering the sensor membrane.

The shield for the blood pump assembly 101 can be configured in other ways. In FIGS. 11-12, the shield includes an additional protective layer covering the sensor membrane. FIG. 11 is a partial side cross-sectional view of another sensing assembly 1100 including an additional protective layer covering the sensor membrane. As shown, the sensing assembly 1100 includes a sensor 1120, a transmission fiber 1124, a jacket 1127, glue 1128, a sensor visor 1122, and a thin layer 1102. The sensor 1120 includes a sensor head 1121, a sensor membrane 1123, and a temperature compensation portion 1142. The sensor head 1121 includes a cavity 1140. The transmission fiber 1124 ends in the proximal portion of the sensor head 1121 to which it is coupled with low loss. The cavity 1140 in combination with the sensor membrane 1123 forms a Fabry-Perot resonator. To allow for the resonant measuring principle, both sides of the cavity 1140 are manufactured to reflect light. As far as detection of the signal has to be made possible, on one side, preferably the transmission fiber 1124 side, partial reflection is realized, and preferably on the sensor membrane 1123 side, full reflection is realized. The temperature compensation portion 1142 is configured to prevent drift in sensed signals due to temperature fluctuations. The temperature compensation portion 1142 is smaller in size than the sensor membrane 1123 and may include silicon dioxide. The jacket 1127 is positioned about the transmission fiber 1124 and may include a glass ring. The transmission fiber 1124 is coupled to the sensor head 1121 by the glue 1128, which may be ultraviolet-curing epoxy. The sensor visor 1122 is configured to extend beyond a distal end of the sensor membrane 1123. The thin layer 1102 is encapsulated over and covers the sensor membrane 1123, and protects the sensor membrane 1123 from damage due to the flow of blood over the sensor membrane 1123. For example, the thin layer 1102 can prevent the sensor membrane 1123 from being dissolved by a chemical reaction with the patient's blood. Additionally, the thin layer 1102 impedes biological deposits from forming directly on the sensor membrane 1123.

The thin layer 1102 may include material capable of being deposited onto the sensor membrane 1123 as a gel and curing. For example, the thin layer 1102 may include silicone. In some embodiments, the thin layer 1102 includes silicon oxide, oxide, metal, metal oxide (such as tantalum pentoxide ($Ta_2O_5$), titanium, or a titanium oxide), or any other coating commonly used in the processing of microelectromechanical systems (MEMS) or semiconductors. The thin layer 1102 can have a thickness of about 1 micron. In some embodiments, the thin layer 1102 has a thickness greater than 1 micron. For example, the thin layer 1102 may have a thickness of 2 microns, 3 microns, 4 microns, 5 microns, >5 microns, or any suitable thickness. In certain embodiments, the thin layer 1102 has a thickness of less than 1 micron. For example, the thin layer 1102 may have a thickness of 0.8 microns, 0.6 microns, 0.4 microns, 0.2 microns, <0.2 microns, or any suitable thickness. In certain embodiments, the protection layer could be several layers to serve as different protection barriers. For example, one layer could be a very thin layer of a metal oxide (such as tantalum pentoxide ($Ta_2O_5$), titanium, or a titanium oxide), silicon oxide, oxide, metal, or any other coating commonly used in the processing of MEMS or semiconductors, and another layer could be an additional polymer protection layer such as a layer of silicone polymer. The very thin layer of metal/metal oxide could be, for example, about 20 nanometers thick. In other embodiments, more than two layers may be preferred to improve adhesion capabilities between the different layers (i.e. silicon, metal, polymer) and provide the desired protection capability. Depending on the stiffness or drift behavior of the materials, different thicknesses might be considered. For materials with stronger negative influence on the signal (e.g., damping, drift, nonlinearity), thin layers will be preferred. For soft protective layers, thicker layers might be preferred to improve the protective function.

FIG. 12 is a partial side cross-sectional view of another sensing assembly 1200 including an additional protective layer covering the sensor membrane. The sensing assembly 1200 includes a sensor 1220, a transmission fiber 1224, a jacket 1227, glue 1228, a sensor visor 1222, and a layer 1202. The sensor 1220 includes a sensor head 1221, a sensor membrane 1223, and a temperature compensation portion 1242. The sensor head 1221 includes a cavity 1240. The transmission fiber 1224 ends in the proximal portion of the sensor head 1221 to which it is coupled with low loss. The cavity 1240 in combination with the sensor membrane 1223 forms a Fabry-Perot resonator. To allow for the resonant measuring principle, both sides of the cavity 1240 are manufactured to reflect light. As far as detection of the signal has to be made possible, on one side, preferably the transmission fiber 1224 side, partial reflection is realized, and preferably on the sensor membrane 1223 side, full reflection is realized. The temperature compensation portion 1242 is configured to prevent drift in sensed signals due to temperature fluctuations. The temperature compensation portion 1242 is smaller in size than the sensor membrane 1223 and may include silicon dioxide. The jacket 1227 is positioned about the transmission fiber 1224 and may include a glass ring. The transmission fiber 1224 is coupled to the sensor head 1221 by the glue 1228, which may be ultraviolet-curing epoxy. The sensor visor 1222 is configured to extend beyond a distal end of the sensor membrane 1223.

The layer 1202 is encapsulated over and covers the sensor membrane 1223, and protects the sensor membrane 1223 from damage due to the flow of blood over the sensor membrane 1223. For example, the layer 1202 can prevent the sensor membrane 1223 from being dissolved by a chemical reaction with the patient's blood. Additionally, the layer 1202 impedes biological deposits from forming directly on the sensor membrane 1223. In embodiments where the sensing assembly 1200 is a pressure sensor, the layer 1202 transmits pressure from the blood to the sensor membrane 1223 so that the blood pressure can be sensed. The layer 1202 may include a material capable of being deposited onto the sensor membrane 1223 as a gel and curing. For example, the layer 1202 may include silicone. The layer 1202 has a thickness of about 0.13 mm. In some embodiments, the layer 1202 has a thickness of about 0.13 mm or greater. For example, the layer 1202 may have a thickness of 0.14 mm, 0.15 mm, 0.16 mm, 0.17 mm, 0.18 mm, 0.19 mm, 0.2 mm, >0.2 mm, or any suitable thickness. In certain embodiments, the layer 1202 has a thickness of about 0.13 mm or less. For example, the layer 1202 may have a thickness of 0.12 mm, 0.11 mm, 0.1 mm, 0.09 mm, 0.08 mm, 0.07 mm, 0.06 mm, 0.05 mm, <0.05 mm, or any suitable thickness. The sensor membrane 1223 is recessed further relative to the sensor visor 1222 in the proximal direction than the sensor membrane 1123 in the embodiment of FIG. 11 by a distance approximately equal to the thickness of the layer 1202. Recessing the sensor membrane 1223 further below the sensor visor 1222 can provide improved protection from damage due to the flow of blood over the sensor membrane 1223. The sensing assembly 1200 can include any number of additional protective layers deposited over the sensor membrane 1223, for example, 1, 2, or 3 protective layers.

The sensing assembly 1200 can also include a gel (e.g., silicone gel) or other material proximal to the sensor membrane 1223 and can partially or fully fill the cavity 1240 to ensure that there is no blood ingress. This can prevent thrombosis in this area of the sensing assembly 1200 and can also prevent damage to the sensing assembly 1200 as blood could potentially damage the transmission fiber 1224 and interfere with its connection with the sensor head 1221.

Figure 13:
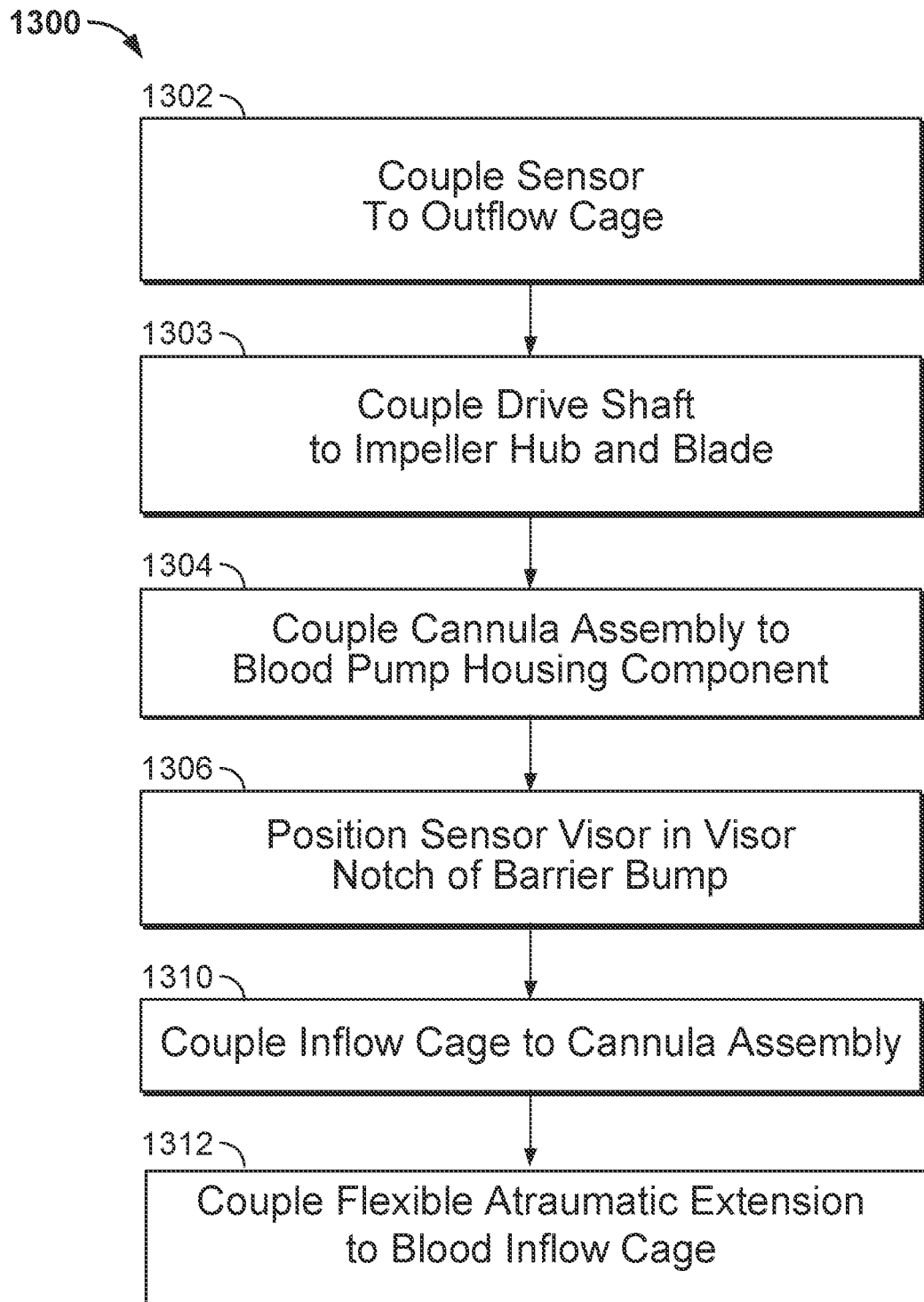
FIG. 13 is a flow diagram of an exemplary process for manufacturing a blood pump assembly.

FIG. 13 is a flow diagram of an exemplary process 1300 for manufacturing a blood pump assembly. At Step 1302, a sensor (e.g., sensor 1020 in FIG. 4) is coupled to a blood pump housing component (e.g., outflow cage 400 of blood pump housing component 103 in FIG. 4), such as using epoxy. Coupling the sensor to the outflow cage of the blood pump housing component may include positioning the sensor into a recess (e.g., recess 122 in FIG. 4) in the blood pump housing component. Alternatively and as previously stated, the sensor can be coupled to a cannula assembly of the blood pump assembly. The sensor includes a sensor membrane (e.g., sensor membrane 1023 in FIG. 4) configured to deflect in response to changes in blood parameters, for example, changes in pressure, flow rate, fluid composition, or viscosity. The sensor membrane is coupled to a transmission fiber (e.g., transmission fiber 1024 in FIG. 4). The sensor includes a sensor visor (e.g., sensor visor 1022 in FIG. 4) extending over the sensor membrane. One or more protective layers (e.g., thin layer 1102 in FIG. 11) may be deposited over the sensor membrane to protect the sensor membrane from damage due to the flow of blood over the sensor membrane. For example, the protective layer can prevent the sensor membrane from being dissolved by a chemical reaction with the patient's blood. Additionally, the protective layer can impede biological deposits from forming directly on the sensor membrane. Alternatively, the protective layer may be thicker than the thin layer 1102 in FIG. 11 (e.g., layer 1202 in FIG. 12) and the sensor membrane may be recessed further below the sensor visor by a distance approximately equal to the thickness of the layer. Recessing the sensor membrane further below the sensor visor can provide improved protection from damage due to the flow of blood over the sensor membrane.

At Step 1303, an impeller hub and blade (e.g., impeller hub 113 and impeller blade 140 of FIG. 6) are coupled to a drive shaft (e.g., drive shaft 104 of FIG. 8) such that the impeller hub and impeller blade rotate as the drive shaft rotates. Alternatively, the impeller hub, blade, and drive shaft can be monolithic and integrally formed. The outflow cage of the blood pump housing component may include one or more output ports (e.g., output ports 125 of FIG. 5) and a plurality of struts (e.g., struts 127 in FIG. 5) extending between the one or more output ports. The recess may be positioned distal to one of the strut of the plurality of struts in the outflow cage of the blood pump housing component.

At Step 1304, a cannula assembly (e.g., cannula assembly 102 in FIG. 1) is coupled to the blood pump housing component. At Step 1306, the sensor visor is positioned in a visor notch of a barrier bump (e.g., visor notch 124 of barrier bump 123 in FIG. 4) which protrudes from the outflow cage of the blood pump housing component. The barrier bump and the sensor visor provide advantages to the sensor in connection with permitting the sensor to traverse the torturous and calcified anatomy of the vascular system and remain operable. At Step 1310, a blood inflow cage (e.g., blood inflow cage 107 of FIG. 1) is coupled to the cannula assembly. At Step 1312, a flexible atraumatic extension (e.g., flexible atraumatic extension 108 of FIG. 1) is coupled to the blood inflow cage.

Figure 14:
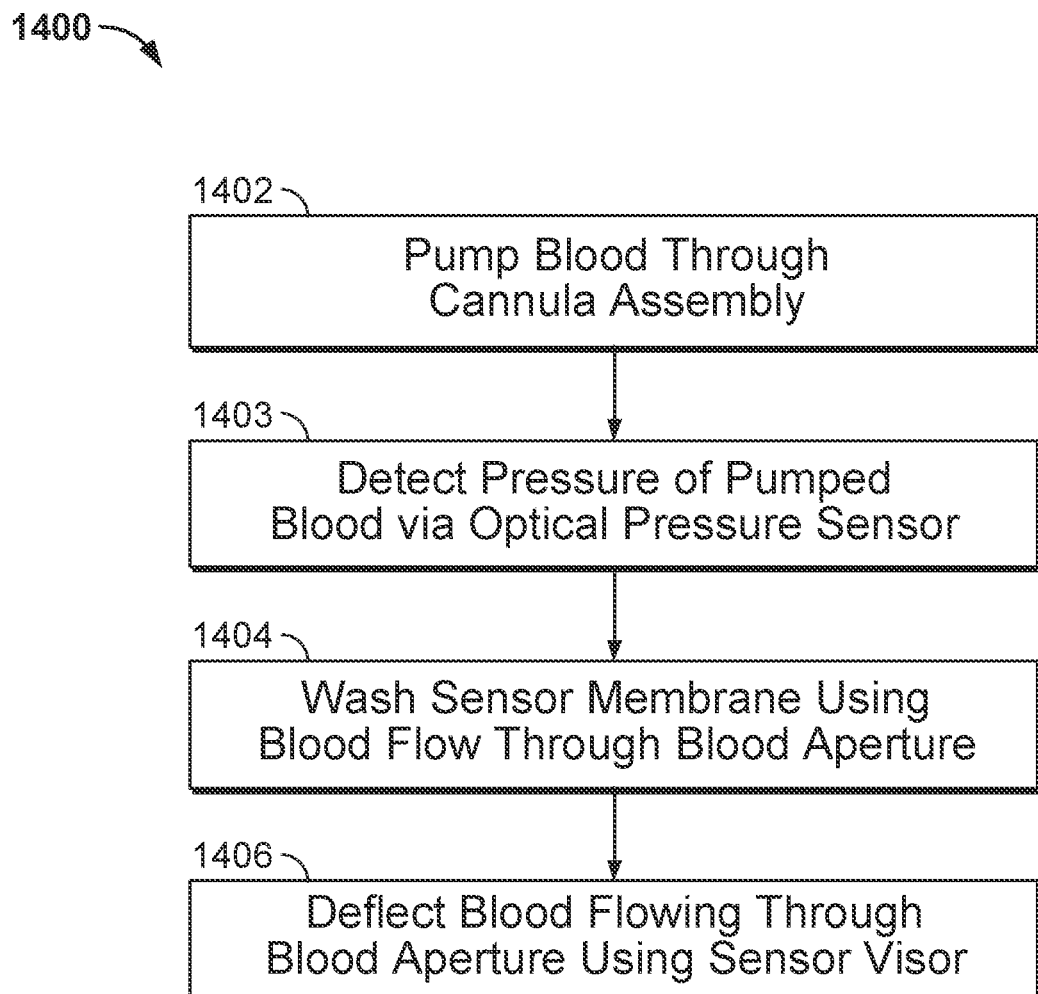
FIG. 14 is a flow diagram of an exemplary process for detecting blood pressure.

FIG. 14 is a flow diagram of an exemplary process 1400 for detecting blood pressure. At Step 1402, blood is pumped through a cannula assembly (e.g., cannula assembly 102 in FIG. 1) using an impeller blade (e.g., impeller blade 140 in FIG. 6) positioned at least in part in the blood pump housing component (e.g., blood pump housing component 103 in FIG. 1). The impeller blade is coupled to an impeller hub (e.g., impeller hub 113 of FIG. 6) rotated by a drive shaft coupled to the impeller hub. The blood pump housing component includes an outflow cage (e.g., outflow cage 400 in FIG. 4). Pumping blood may include pumping blood through one or more output ports (e.g., output port 125 in FIG. 4) in the blood pump housing component.

At Step 1403, blood pressure of the pumped blood is detected using an optical pressure sensor (e.g., sensor 1020 in FIG. 4) coupled to the outflow cage of the blood pump housing component. The optical pressure sensor includes a sensor membrane (e.g., sensor membrane 1023 in FIG. 4) configured to deflect in response to a change in pressure on the sensor membrane. The sensor membrane may include a glass/silicon material. The sensor membrane may be facing toward a distal end of the blood pump assembly. The sensor membrane may have a thickness as previously described. The optical pressure sensor includes a sensor visor (e.g., sensor visor 1022 in FIG. 4) extending a distance in the distal direction beyond the sensor membrane so as to form a shroud portion overhanging the sensor membrane. The outflow cage of the blood pump housing component may include a barrier bump (e.g., barrier bump 123 in FIG. 4) protruding from the outflow cage of the blood pump housing component. The barrier bump and the sensor visor provide advantages to the optical pressure sensor in connection with permitting the optical pressure sensor to traverse the torturous and calcified anatomy of the vascular system and remain operable. The barrier bump may protect the sensor membrane by deflecting upcoming obstacles presented by calcification within the vascular system or changes in direction of the sensor. The sensor visor may protect the sensor membrane by preventing soft obstructions, such as valve leaves on a blood pump introducer, from contacting and damaging the sensor membrane. Obstacles deflected by the barrier bump may ride over the sensor visor, thereby preventing the obstacles from contacting and/or damaging the sensor membrane. The barrier bump may be positioned in front of a recess (e.g., recess 122 in FIG. 4). The recess may be between the barrier bump and the sensor membrane.

A protective layer (e.g., thin layer 1102 in FIG. 11) or layers may be deposited over the sensor membrane to protect the sensor membrane from damage due to the flow of blood over the sensor membrane. For example, the layers can prevent the sensor membrane from being dissolved by a chemical or biological reaction with the patient's blood. Additionally, the layer can impede biological deposits from forming directly on the sensor membrane. Alternatively, the protective layer may be thicker than the thin layer 1102 in FIG. 11 (e.g., layer 1202 in FIG. 12) and the sensor membrane may be recessed further below the sensor visor by a distance approximately equal to the thickness of the layer. Recessing the sensor membrane below the sensor visor can provide improved protection from damage due to the flow of blood over the sensor membrane. In the case of an optical sensor, the sensor is coupled directly or indirectly to an optical fiber (e.g., transmission fiber 1024 in FIG. 4).

At Step 1404, the sensor membrane is washed by blood flowing through a blood aperture (e.g., blood aperture 136 of FIG. 4) extending through the outflow cage of the blood pump housing component. Washing the sensor membrane prevents buildup or clotting of blood on the surface of the sensor membrane.

At Step 1406, blood flowing through the blood aperture is deflected using the sensor visor which can extend from the optical pressure sensor over the sensor membrane and into a visor notch in the barrier bump. The blood can also exit through the blood aperture and a new volume of blood can enter the blood aperture.

The foregoing is merely illustrative of the principles of the disclosure, and the systems, methods, and devices can be practiced by other than the described embodiments, which are presented for purposes of illustration and not of limitation. It is to be understood that the systems, devices, and methods disclosed herein, while shown for use in blood pump assemblies that may be introduced percutaneously during a cardiac procedure through the vascular system, may be applied to systems, devices, and methods to be used in other types of therapy and devices requiring sensors.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A method of detecting blood pressure comprising:
   pumping blood through a cannula assembly coupled to a blood pump housing component, the blood pumped by an impeller blade positioned at least in part in the blood pump housing component, the impeller blade rotated by a drive unit coupled to the impeller blade, the blood pump housing component including a peripheral wall extending about a rotational axis of the impeller blade; and
   detecting a blood pressure of the blood pumped using an optical pressure sensor coupled to the peripheral wall of the blood pump housing component, the optical pressure sensor including a sensor membrane configured to deflect in response to a change in pressure on the sensor membrane, the sensor membrane coupled to an optical fiber, and the optical pressure sensor including a sensor visor overhanging the sensor membrane.

2. The method of claim 1, further comprising washing the sensor membrane using blood flow through a blood aperture extending through the peripheral wall of the blood pump housing component, the blood aperture positioned in a blood recess positioned in front of the sensor membrane of the optical pressure sensor.

3. The method of claim 2, wherein the peripheral wall of the blood pump housing component includes a barrier bump protruding from the peripheral wall of the blood pump housing component, the barrier bump positioned in front of the blood recess, such that the blood recess is between the barrier bump and the sensor membrane.

4. The method of claim 3, further comprising deflecting the blood flowing through the blood aperture using the sensor visor positioned in a visor notch in the barrier bump.

5. The method of claim 2, wherein the blood aperture has smooth surfaces to prevent thrombosis.

6. The method of claim 2, wherein the blood recess is wider than the optical pressure sensor.

7. The method of claim 1, wherein pumping blood includes pumping blood through one or more blood exhaust windows in the blood pump housing component.

8. The method of claim 1, wherein the sensor membrane comprises a glass material.

9. The method of claim 1, wherein the sensor membrane has a thickness of about 2 microns or less.

10. The method of claim 1, further comprising transmitting, through the optical fiber, a signal sensed by the optical pressure sensor to a processor for detecting the blood pressure.

11. The method of claim 10, wherein the optical pressure sensor comprises a glass ring positioned about the optical fiber.

\* \* \* \* \*